(12) United States Patent
Musselman

(10) Patent No.: US 8,901,488 B1
(45) Date of Patent: Dec. 2, 2014

(54) ROBUST, RAPID, SECURE SAMPLE MANIPULATION BEFORE DURING AND AFTER IONIZATION FOR A SPECTROSCOPY SYSTEM

(75) Inventor: Brian D. Musselman, Melrose, MA (US)

(73) Assignee: Ionsense, Inc., Saugus, MA (US)

( * ) Notice: Subject to any disclaimer, the term of this patent is extended or adjusted under 35 U.S.C. 154(b) by 287 days.

(21) Appl. No.: 13/449,615

(22) Filed: Apr. 18, 2012

Related U.S. Application Data

(60) Provisional application No. 61/476,380, filed on Apr. 18, 2011.

(51) Int. Cl.
*H01J 49/00* (2006.01)
*G01N 33/543* (2006.01)

(52) U.S. Cl.
CPC ................. *G01N 33/54326* (2013.01)
USPC ............ 250/288; 250/281; 250/282

(58) Field of Classification Search
CPC ........... G01N 33/54326; B01L 2400/043; B01L 2200/0647; B03C 1/01
USPC ........................................ 250/288
See application file for complete search history.

(56) References Cited

U.S. PATENT DOCUMENTS

| | | | |
|---|---|---|---|
| 3,633,027 A | 1/1972 | Rhyage |
| 3,957,470 A | 5/1976 | Dawes |
| 4,016,421 A | 4/1977 | Hull |
| 4,144,451 A | 3/1979 | Kambara |
| 4,213,326 A | 7/1980 | Brodasky |
| 4,542,293 A | 9/1985 | Fenn |
| 4,546,253 A | 10/1985 | Tsuchiya |
| 4,654,052 A | 3/1987 | Sharp |
| 4,861,988 A | 8/1989 | Henion |
| 5,012,052 A | 4/1991 | Hayes |
| 5,055,677 A | 10/1991 | Amirav |
| 5,137,553 A | 8/1992 | Dawes |
| 5,192,865 A | 3/1993 | Zhu |

(Continued)

FOREIGN PATENT DOCUMENTS

| | | |
|---|---|---|
| DE | 102007015542 | 10/2007 |
| GB | 2263578 | 7/1993 |

(Continued)

OTHER PUBLICATIONS

Chen, et al ("Fe3O4/TiO2 Core/Shell Nanoparticles as Affinity Probes for the Analysis of Phosphopeptides Using TiO2 Surface-Assisted Laser Desorption/Ionization Mass Spectrometry" Anal. Chem. vol. 77, No. 8, pp. 5912-5919, 2005).*

(Continued)

*Primary Examiner* — Michael Maskell
(74) *Attorney, Agent, or Firm* — Sci-Law Strategies, PC

(57) ABSTRACT

This invention provides for the efficient positioning of a sample to be analyzed by using either magnetic or electro-mechanical fields to retain the sample in the ionization region. In an embodiment of the present invention, the sample is contacted with a sampler device, which is inserted into a chamber and accurately positioned using electro-mechanical devices. In an embodiment of the invention, the influence of an electro-mechanical field on the sampler device enables the sample to be positioned in the ionization region to be contacted by particles that result in ionization of the sample whereby rendering the resulting ions available for analysis.

20 Claims, 11 Drawing Sheets

(56) References Cited

U.S. PATENT DOCUMENTS

| | | |
|---|---|---|
| 5,306,412 A | 4/1994 | Whitehouse |
| 5,352,892 A | 10/1994 | Mordehai |
| 5,367,163 A | 11/1994 | Otsuka |
| 5,381,008 A | 1/1995 | Tanner |
| 5,412,208 A | 5/1995 | Covey |
| 5,448,062 A | 9/1995 | Cooks |
| 5,552,599 A | 9/1996 | Giessmann |
| 5,559,326 A | 9/1996 | Goodley |
| 5,614,711 A | 3/1997 | Li |
| 5,624,537 A | 4/1997 | Turner |
| 5,684,300 A | 11/1997 | Taylor |
| 5,736,741 A | 4/1998 | Bertsch |
| 5,788,166 A | 8/1998 | Valaskovic |
| 5,868,322 A | 2/1999 | Loucks, Jr. |
| 5,959,297 A | 9/1999 | Weinberg |
| 5,997,746 A | 12/1999 | Valaskovic |
| 6,107,628 A | 8/2000 | Smith |
| 6,124,675 A | 9/2000 | Betrand |
| 6,190,559 B1 | 2/2001 | Valaskovic |
| 6,225,623 B1 | 5/2001 | Turner |
| 6,297,499 B1 | 10/2001 | Fenn |
| 6,359,275 B1 | 3/2002 | Bertsch |
| 6,395,183 B1 | 5/2002 | Valaskovic |
| 6,562,211 B1 | 5/2003 | Kunnecke |
| 6,583,408 B2 | 6/2003 | Smith |
| 6,600,155 B1 | 7/2003 | Andrien, Jr. |
| 6,646,256 B2 | 11/2003 | Gourley |
| 6,649,907 B2 | 11/2003 | Ebeling |
| 6,670,608 B1 | 12/2003 | Taylor |
| 6,690,006 B2 | 2/2004 | Valaskovic |
| 6,717,139 B2 | 4/2004 | Taniguchi |
| 6,723,985 B2 | 4/2004 | Schultz |
| 6,744,041 B2 | 6/2004 | Sheehan |
| 6,744,046 B2 | 6/2004 | Valaskovic |
| 6,784,424 B1 | 8/2004 | Willoughby |
| 6,803,565 B2 | 10/2004 | Smith |
| 6,806,468 B2 | 10/2004 | Laiko |
| 6,818,889 B1 | 11/2004 | Sheehan |
| 6,861,647 B2 | 3/2005 | Reilly |
| 6,878,930 B1 | 4/2005 | Willoughby |
| 6,888,132 B1 | 5/2005 | Sheehan |
| 6,914,243 B2 | 7/2005 | Sheehan |
| 6,943,347 B1 | 9/2005 | Willoughby |
| 6,949,739 B2 | 9/2005 | Franzen |
| 6,949,740 B1 | 9/2005 | Sheehan |
| 6,949,741 B2 | 9/2005 | Cody |
| 6,956,205 B2 | 10/2005 | Park |
| 6,977,372 B2 | 12/2005 | Valaskovic |
| 6,979,816 B2 | 12/2005 | Tang |
| 6,992,299 B2 | 1/2006 | Lee |
| 7,015,466 B2 | 3/2006 | Takats |
| 7,064,317 B2 * | 6/2006 | McLuckey et al. ........... 250/282 |
| 7,081,618 B2 | 7/2006 | Laprade |
| 7,081,621 B1 | 7/2006 | Willoughby |
| 7,095,019 B1 | 8/2006 | Sheehan |
| 7,112,785 B2 | 9/2006 | Laramee |
| 7,138,626 B1 | 11/2006 | Karpetsky |
| 7,161,145 B2 | 1/2007 | Oser |
| 7,196,525 B2 | 3/2007 | Sparkman |
| 7,253,406 B1 | 8/2007 | Sheehan |
| 7,423,261 B2 | 9/2008 | Truche |
| 7,429,731 B1 | 9/2008 | Karpetsky |
| 7,544,933 B2 | 6/2009 | Cooks |
| 7,569,812 B1 | 8/2009 | Karpetsky |
| 7,700,913 B2 | 4/2010 | Musselman |
| 7,705,297 B2 | 4/2010 | Musselman |
| 7,714,281 B2 | 5/2010 | Musselman |
| 7,777,181 B2 | 8/2010 | Musselman |
| 7,893,408 B2 | 2/2011 | Hieftje |
| 7,928,364 B2 | 4/2011 | Musselman |
| 7,929,138 B1 | 4/2011 | Webb |
| 8,026,477 B2 | 9/2011 | Musselman |
| 8,044,346 B2 | 10/2011 | Kostiainen |
| RE43,078 E | 1/2012 | Cody et al. |
| 8,217,341 B2 | 7/2012 | Musselman |
| 2002/0005478 A1 | 1/2002 | Hillenkamp |
| 2002/0121596 A1 | 9/2002 | Laiko |
| 2002/0185593 A1 | 12/2002 | Doring |
| 2002/0185595 A1 | 12/2002 | Smith |
| 2002/0185606 A1 | 12/2002 | Smith |
| 2003/0052268 A1 | 3/2003 | Doroshenko |
| 2004/0094706 A1 | 5/2004 | Covey |
| 2004/0129876 A1 | 7/2004 | Franzen |
| 2004/0159784 A1 | 8/2004 | Doroshenko |
| 2004/0169137 A1 | 9/2004 | Westphall |
| 2005/0079631 A1 | 4/2005 | Laiko |
| 2005/0230635 A1 | 10/2005 | Takats |
| 2005/0236374 A1 | 10/2005 | Blankenship |
| 2005/0236565 A1 | 10/2005 | Oser |
| 2006/0071665 A1 | 4/2006 | Blake |
| 2006/0079002 A1 | 4/2006 | Gologan |
| 2006/0097157 A1 | 5/2006 | Ouyang |
| 2006/0163468 A1 | 7/2006 | Wells |
| 2006/0249671 A1 | 11/2006 | Karpetsky |
| 2006/0266941 A1 | 11/2006 | Vestal |
| 2007/0114389 A1 | 5/2007 | Karpetsky |
| 2007/0187589 A1 | 8/2007 | Cooks |
| 2007/0228271 A1 | 10/2007 | Truche et al. |
| 2007/0278397 A1 | 12/2007 | Bateman |
| 2008/0073548 A1 | 3/2008 | Denton |
| 2008/0156985 A1 | 7/2008 | Venter |
| 2008/0202915 A1 | 8/2008 | Hieftje |
| 2008/0217254 A1 * | 9/2008 | Anderson ..................... 210/695 |
| 2009/0272893 A1 | 11/2009 | Hieftje |
| 2010/0078550 A1 | 4/2010 | Wiseman |
| 2010/0102222 A1 | 4/2010 | Musselman |
| 2010/0140468 A1 | 6/2010 | Musselman |
| 2010/0294925 A1 | 11/2010 | Musselman |
| 2010/0301209 A1 | 12/2010 | Ouyang |
| 2011/0042560 A1 | 2/2011 | Ouyang |
| 2011/0101216 A1 | 5/2011 | Musselman |
| 2012/0006983 A1 | 1/2012 | Cody |
| 2012/0145890 A1 | 6/2012 | Goodlett et al. |
| 2012/0199735 A1 | 8/2012 | Krechmer |
| 2012/0322683 A1 * | 12/2012 | Liu et al. ........................ 506/9 |
| 2013/0273552 A1 * | 10/2013 | Ohashi ..................... 435/6.12 |
| 2014/0024822 A1 * | 1/2014 | Connolly et al. ............ 536/25.4 |

FOREIGN PATENT DOCUMENTS

| | | |
|---|---|---|
| JP | 50-106694 | 8/1975 |
| JP | 51-120288 | 10/1976 |
| JP | 52-91494 | 8/1977 |
| JP | 60-41748 | 3/1985 |
| JP | 2005-150027 | 6/2005 |
| WO | WO03025973 | 3/2003 |
| WO | WO03081205 | 10/2003 |
| WO | WO2004068131 | 8/2004 |
| WO | WO2005094389 | 10/2005 |
| WO | WO2005104182 | 11/2005 |
| WO | WO2007/103693 | 9/2007 |
| WO | WO2007/140349 | 12/2007 |
| WO | WO2007/140351 | 12/2007 |
| WO | WO2008/046111 | 4/2008 |
| WO | WO2008/054393 | 5/2008 |
| WO | WO2008/082603 | 7/2008 |
| WO | WO2009/023361 | 2/2009 |
| WO | WO2011/072130 | 6/2011 |
| WO | WO2011/106656 | 9/2011 |

OTHER PUBLICATIONS

Barber, M. et al., "Fast atom bombardment of solids (F.A.B.): a new ion source for mass spectrometry" J.Chem. Soc. Chem. Commun., 1981, 325.

Cody, R.B. et al., "Versatile New Ion Source for the Analysis of Materials in Open Air under Ambient Conditions" Anal. Chem., 2005, 77, 2297-2302.

Cooks, R.G. et al., "Ambient Mass Spectrometry", Science, 2006, 311, 1566-1570.

Dalton, C.N. et al., "Electrospray-Atmospheric Sampling Glow Discharge Ionization Source for the Direct Analysis of Liquid Samples", Analytical Chemistry, Apr. 1, 2003, vol. 75, No. 7, pp. 1620-1627.

(56) References Cited

OTHER PUBLICATIONS

Fenn et al., "Electrospray Ionization for Mass Spectrometry of Large Biomolecules," Science, vol. 246, No. 4926, Oct. 6, 1989, pp. 64-71.
Guzowski, J.P. Jr. et al., "Development of a Direct Current Gas Sampling Glow Discharge Ionization Source for the Time-of-Flight Mass Spectrometer", J. Anal. At. Spectrom., 14, 1999, pp. 1121-1127.
Haddad, R., et al., "Easy Ambient Sonic-Spray Ionization Mass Spectrometry Combined with Thin-Layer Chromatography," *Analytical Chemistry*, vol. 80, No. 8, Apr. 15, 2008, pp. 2744-2750.
Hill, C.A. et al., "A pulsed corona discharge switchable high resolution ion mobility spectrometer-mass spectrometer", Analyst, 2003, 128, pp. 55-60.
Hiraoka, K. et al., "Atmospheric-Pressure Penning Ionization Mass Spectrometry", Rapid Commun. Mass Spectrom., 18, 2004, pp. 2323-2330.
Hites, Gas Chromatography Mass Spectrometry, Chapter 39, Jun. 24, 1997, pp. 609-626.
Karas, M. et al., "Laser desorption ionization of proteins with molecular masses exceeding 10,000 daltons" Anal. Chem. 1988, 60, 2299-2301.
Kauppila, T.J. et al., "Desorption atmospheric pressure photoionization—mass spectrometry in routine analysis of confiscated drugs" Forensic Science Int., 2011, 210, 206-212.
Kojiro, D.R. et al., "Determination of $C_1$-$C_4$ Alkanes by Ion Mobility Spectrometry", Anal. Chem., 63, 1991, pp. 2295-2300.
Leymarie, N. et al., "Negative Ion Generation Using a MAB Source", presented at the Annual Meeting of the American Society of Mass Spectrometry, 2000.
McLuckey, S.A. et al., "Atmospheric Sampling Glow Discharge Ionization Source for the Determination of Trace Organic Compounds in Ambient Air", Anal. Chem., 60, 1988, pp. 2220-2227.
Otsuka, K. et al., "An Interface for Liquid Chromatograph/Liquid Ionization Mass Spectrometer", Analytical Sciences, Oct. 1988, vol. 4, pp. 467-472.
Takáts et al., "Mass Spectrometry Sampling Under Ambient Conditions with Desorption Electrospray Ionization," Science, vol. 306, No. 5695, Oct. 15, 2004, pp. 471-473.
Tanaka, K. et al., "Protein and polymer analyses up to m/z 100,000 by laser ionization time-of-flight", Rapid Commun. Mass Spectrom., 1988, 2, 151-153.
Tembreull, R., et al., "Pulsed Laser Desorption with Resonant Two-Photon Ionization Detection in Supersonic Beam Mass Spectrometry," Anal. Chem., vol. 58, 1986, pp. 1299-1303, p. 1299.
Zhao, J. et al., Liquid Sample Injection Using an Atmospheric Pressure Direct Current Glow Discharge Ionization Source, Analytical Chemistry, Jul. 1, 1992, vol. 64, No. 13, pp. 1426-1433.
International Search Report for Int'l Application No. PCT/US07/63006.
International Search Report for Int'l Application No. PCT/US07/69821.
International Search Report for Int'l Application No. PCT/US07/69823.
International Search Report for Int'l Application No. PCT/US07/81439.
Supplementary European Search Report dated Jan. 7, 2010 in Application No. 07757665.0 PCT/US2007/063006, 8 pages.
Supplementary European Search Report dated Mar. 10, 2010 in Application No. 07797812.0 PCT/US2007/069823, 9 pages.
Supplementary European Search Report dated Mar. 25, 2010 in Application No. 07797811.2 PCT/US2007/069821, 9 pages.
Supplementary European Search Report dated Mar. 10, 2010 in Application No. 07844307.4 PCT/US2007/081439, 12 pages.
Japanese Office Action dated Jan. 19, 2012 in Application No. 2008-558459 PCT/US2007/063006, 4 pages.
Unofficial Translation of Japanese Office Action dated Jan. 19, 2012 in Application No. 2008-558459 PCT/US2007/063006, 5 pages.
Chinese Office Action dated Feb. 2, 2012 in Application No. 200780015974.5 PCT/US2007/063006, 5 pages.
Article 94(3) European Communication dated Mar. 14, 2012 in Application No. 07757665.0 PCT/US2007/063006, 9 pages.

\* cited by examiner

US 8,901,488 B1

ROBUST, RAPID, SECURE SAMPLE MANIPULATION BEFORE DURING AND AFTER IONIZATION FOR A SPECTROSCOPY SYSTEM

PRIORITY CLAIM

This application claims priority to U.S. Provisional Patent Application Ser. No. 61/476,380 entitled: "ROBUST, RAPID, SECURE SAMPLE MANIPULATION BEFORE DURING AND AFTER IONIZATION FOR A SPECTROSCOPY SYSTEM", inventor: Brian D. Musselman, and filed Apr. 18, 2011. This application is herein expressly incorporated by reference in its entirety.

FIELD OF THE INVENTION

The present invention permits desorption ionization of powders, plant materials, and loose substances by securing the position of these materials which are otherwise easily displaced during sample handling and analysis.

BACKGROUND OF THE INVENTION

Ambient pressure desorption ionization sources, such as direct analysis in real time (DART®) and desorption electrospray ionization, enable detection of chemicals present as or embedded in a solid object or condensed on surfaces. Examples of sources include: using a flowing heated gas containing metastable atoms or molecules in DART, using a flowing gas containing ions and metastable atoms or molecules in Flowing Atmospheric Pressure Afterglow (FAPA), and using a flowing high pressure mixture of gas and solvent droplets in desorption electrospray ionization (DESI).

A common occurrence in Homeland Security associated 'security alerts' is the report describing the presence of a "white powder". Identification of such materials requires a determination of composition. Enabling direct determination of composition without the requirement for dissolving the material facilitates reduced sample handling and thus affords greater protection to the humans undertaking the analysis as well as reduced time for analysis.

SUMMARY OF THE INVENTION

In various embodiments of the present invention, metal powders are used to disperse and retain samples for analysis. In an embodiment of the invention, a device for ionizing a sample comprises a sampler device for maintaining or constraining the position of the sample relative to the flowing gases and liquids exiting an ionization source. The device further includes a chamber or open region where the sample can be positioned and an entrance into a spectroscopy system where analysis occurs.

BRIEF DESCRIPTION OF THE DRAWINGS

This invention is described with respect to specific embodiments thereof. Additional features can be appreciated from the Figures in which.

DETAILED DESCRIPTION OF THE INVENTION

Figure 1:
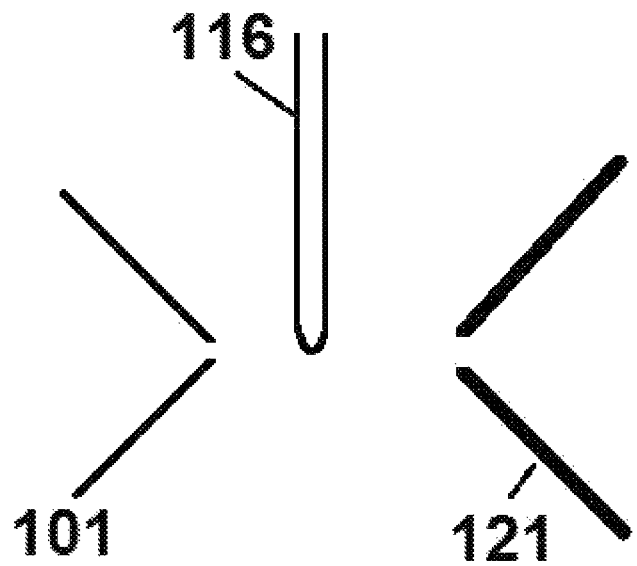
FIG. 1 shows a schematic diagram of a prior art sample device.

The development of efficient desorption ionization sources for use with spectroscopy systems has enabled rapid analysis of samples without requiring laborious sample preparation. These desorption ionization sources require that the sample be positioned in a small region at the exit of the source to permit interaction of the ionizing gases with the sample for analysis.

Atmospheric pressure desorption ionization sources such as direct analysis real time (DART®) and desorption electrospray ionization function well for the ionization of solids and samples adsorbed onto surfaces because they can be fixed in position and not displaced by the action of the flowing gases and solvents. Once formed the ions can, for example, be introduced into a mass spectrometer for mass analysis. However, in the case of chemicals present in powder form, the direct desorption ionization analysis can become problematic due to displacement of the powder by the action of the flowing gases and liquids utilized in the experiment. Without retention of the sample in the desorption ionization region, analysis of these compounds is either compromised and/or results in contamination of the spectroscopy system as the desorbed chemicals contaminate surfaces and entrances to the spectroscopy system.

Thus, for loose powders the utility of the desorption ionization technology is reduced since powders and other light weight or loose samples often cannot be anchored without altering their chemical state (e.g., making into a solution). In an embodiment of the present invention, a simple method to retain powder type samples for surface desorption ionization at atmospheric pressure with increased certainty, involves the co-mixing and thereby the dispersal of a heavy weight powder with the sample powder prior to analysis in order to secure the powder in position. In an embodiment of the present invention, the heavy weight powder can be a metal powder. In an embodiment of the invention, the sample with the metal powder dispersed and therefore coating the sample can be maintained in its position by the weight of the metal powder. In an alternative embodiment of the present invention, the sample with the metal powder dispersed and thereby coating the sample can be maintained in its position by a magnetic field used to fix the metal in position for analysis. In an embodiment of the present invention, a device provides the means for positioning of a sample powder in a desorption ionization region.

In various embodiments of the invention, the metal powder or granules can be selected from the group consisting of metals and non-metals. In various embodiments of the invention, the powder or granules can be selected from the group consisting of magnetic and non-magnetic metals. In various embodiments of the invention, the powder or granules can be one or both a paramagnetic and a ferromagnetic material.

Paramagnetism is a form of magnetism which occurs only in the presence of an externally applied magnetic field. Ferromagnetism is the mechanism by which certain materials form permanent magnets or are attracted to magnets. Classical electro-magnetism indicates that two nearby magnetic dipoles will tend to align in opposite directions, so their magnetic fields will oppose one another and cancel out. However, in ferromagnetic materials the dipoles tend to align in the same direction. The Pauli Exclusion Principle teaches that two electrons with the same spin cannot also have the same 'position'. Under certain conditions, the Pauli Exclusion Principle can be satisfied if the position of the outer orbitals of the aligned electrons is sufficiently distant. In these ferromagnetic materials, the electrons having parallel spins result in the distribution of electric charge in space being further apart and therefore the energy of these systems is at a minimum. The unpaired electrons align in parallel to an external magnetic field in paramagnetic materials. Only atoms with partially filled shells can have a net magnetic moment, so ferromagnetism and paramagnetism only occur in materials with partially filled outer electron shells. Non-magnetic metals typically have filled outer electron shells (e.g., Beryllium, Cadmium, Calcium, Magnesium, Mercury, and Zinc) or form covalently bound molecules fulfilling this condition (e.g., Aluminum, Barium, Copper, Gold, Lead, Lithium, Platinum, Potassium, Radium, Rhodium, Strontium, Silver, Tin, Titanium and Tungsten). As the temperature of ferromagnetic materials increase, the entropy of the system reduces the ferromagnetic alignment of the dipoles. When the temperature rises above the Curie temperature, the system can no longer maintain spontaneous magnetization, although the material still responds paramagnetically to an external field (see Table I for list of ferromagnetic and ferrimagnetic materials and their Curie temperature).

TABLE I

List of ferromagnetic and ferrimagnetic materials and their Curie temperature

| Material | Curie temperature (° K) |
|---|---|
| Co | 1388 |
| Fe | 1043 |
| $FeOFe_2O_3$ | 858 |
| $NiOFe_2O_3$ | 858 |
| $CuOFe_2O_3$ | 728 |
| $MgOFe_2O_3$ | 713 |
| MnBi | 630 |

TABLE I-continued

List of ferromagnetic and ferrimagnetic materials and their Curie temperature

| Material | Curie temperature (° K) |
|---|---|
| Ni | 627 |
| MnSb | 587 |
| $MnOFe_2O_3$ | 573 |
| $Y_3Fe_5O_{12}$ | 560 |
| $CrO_2$ | 386 |
| MnAs | 318 |
| Gd | 292 |
| Dy | 88 |
| EuO | 69 |

In various embodiments of the invention, the powder or granules can be selected from the group consisting of one or more iron containing substances including Fe, FeO, $FeOFe_2O_3$, $Fe_2O_3$, $MnOFe_2O_3$, $MgOFe_2O_3$, $Y_3Fe_5O_{12}$ and $Fe_3O_4$. In various embodiments of the invention, the powder or granules can be selected from the group consisting of one or more copper containing substances including Cu, CuO, $CuOFe_2O_3$ and $Cu_2O$. In various embodiments of the invention, the powder or granules can be selected from the group consisting of one or more aluminum containing substances including Al and $Al_2O_3$. In various embodiments of the invention, the powder or granules can be selected from the group consisting of one or more nickel containing substances including Ni, NiO, $Ni_2O_3$, $Ni(OH)_2$ and $NiOFe_2O_3$. In various embodiments of the invention, the powder or granules can be selected from the group consisting of one or more cobalt containing substances including Co, $NaCoO_2$ and $Co_3O_4$. In various embodiments of the invention, the powder or granules can be selected from the group consisting of one or more lanthanide metals. In various embodiments of the invention, the powder or granules can be selected from the group consisting of one or more ferromagnetic and/or ferrimagnetic materials of Table I. In various embodiments of the invention, the powder or granules can be selected from the group consisting of physical mixing of two or more of Fe, FeO, $FeOFe_2O_3$, $Fe_2O_3$, $Fe_3O_4$, Cu, CuO, and $Cu_2O$, Al and $Al_2O_3$. In various embodiments of the invention, the powder or granules can be selected from a physical combination of two or more metals or alloys that can either be magnetic or non-magnetic.

When a security alert reports the presence of a "white powder" or other unknown substance, there is an immediate and real need for determining the composition of the powder and specifically whether the powder is anthrax or any other dangerous biological or chemical agent. The first step in analysis of these 'unknowns' often involves isolation of the material in specialized containers for transfer to protect the analyst and his or her environment from contamination. In order to determine the chemical composition or organism present in the powder, the analyst often creates a soluble solution by dissolving the powder in water or an appropriate solvent. The use of expensive and often elaborate testing equipment is needed when using such a soluble solution and since not all powders are soluble valuable time is lost as the analyst labors to create that solution. Ultimately, the sample represents no security threat but the time used in determination of its composition is lengthened by each step of manipulation.

The challenge to rapid chemical analysis is designing a process that uses a minimum of sample manipulation in order to complete chemical analysis in mere seconds. The ability to complete rapid analysis of the sample can be facilitated if real time ionization can be used as a screening method. Thus, the development of a more practical device for positioning samples with minimal human intervention can be an important requirement for deploying real time monitoring, beyond the confines of the laboratory. Utilizing metal powders with ionization techniques to sample and retain the 'unknown' powder and subsequently permit its positioning for analysis can provide a means to facilitate the rapid determination of composition which is necessary to either dismiss or elevate the threat level.

A vacuum of atmospheric pressure is 1 atmosphere=760 torr. Generally, 'approximately' in this pressure range encompasses a range of pressures from below $10^1$ atmosphere=7.6× $10^3$ torr to $10^{-1}$ atmosphere=7.6×$10^1$ torr. A vacuum of below $10^{-3}$ torr would constitute a high vacuum. Generally, 'approximately' in this pressure range encompasses a range of pressures from below $5\times10^{-3}$ torr to $5\times10^{-6}$ torr. A vacuum of below $10^{-6}$ torr would constitute a very high vacuum. Generally, 'approximately' in this pressure range encompasses a range of pressures from below $5\times10^{-6}$ torr to $5\times10^{-9}$ torr. In the following, the phrase 'high vacuum' encompasses high vacuum and very high vacuum. The sampler/chamber system can be at atmospheric pressure.

Movement of Samples into and Through the Ionization Region for Analysis

In atmospheric pressure desorption ionization experiments solid objects placed in close proximity to the exit of the source interact with the gas exiting that source. The solid object is often positioned manually or by using devices such as tweezers. In an embodiment of the present invention, a sample in powder form can be immersed into or deposited into a container for co-mixing with metal powder. After mixing to disperse the powder in with the metal, a small fraction of the sample can be removed from the tube along with the metal, enabling its analysis as it is placed in the desorption ionization region. For rapid qualitative determination of samples, the quantity of sample retained on the metal is not critical; therefore, the acquisition of even a small quantity of material can enable a successful analysis. In an alternative embodiment of the present invention, automation of the sampling technology for desorption ionization involves fabrication of a partially glass and partially metal rod sampler tip to which a small magnet can be fixed to cause the magnetized metal coated with "unknown" powder to be retained in its position for analysis. In another embodiment of the invention, by using a microscope slide-sized flat surface (i.e. a flat surface the size of a microscope slide) to which one or more magnets have been fixed on the underside, the metal coated with powder can be deposited on the surface for analysis. In a variety of embodiments of the invention, electro-magnetic fields can be used to automate the movement of the sample from container to container or from container to sample surface for analysis. In an embodiment of the invention, a non-magnetic metal coated with powder can be deposited onto a surface for analysis where the weight of the metal can be sufficient to cause the sample to maintain position in the presence of the flowing gas stream used for desorption ionization.

In an embodiment of the present invention, the mixing of a metal powder with an 'unknown' powder or 'unknown' sample present in crystalline form facilitates mechanical control of the positioning of the sample with magnetic or electro-magnetic fields. A 'sampler device' can be fabricated such that the sample can be inserted into an enclosed chamber attached to a desorption ionization region. Using the 'sampler device' the sample can be reliably transferred from the enclosed chamber into the desorption ionization region by mechanical or electro-mechanical means. In an embodiment of the invention a method is described for depositing the 'unknown' or material of interest onto a sampler and dropping the sampler into the chamber and subsequently manipulating the sampler into position using robotics without requiring human intervention to physically touch or contact the sample. Once the sample is placed in the desorption ionization region, chemical analysis can take place.

A mechanical device is operated by a mechanism. An electro-mechanical device or system is a mechanical device or system that is actuated or controlled by electricity. An electro-magnetic device is operated, actuated or controlled by magnetism produced by electricity. An electro-mechanical force is a force formed by electro-magnetic induction.

Sampler Device

Figure 2:
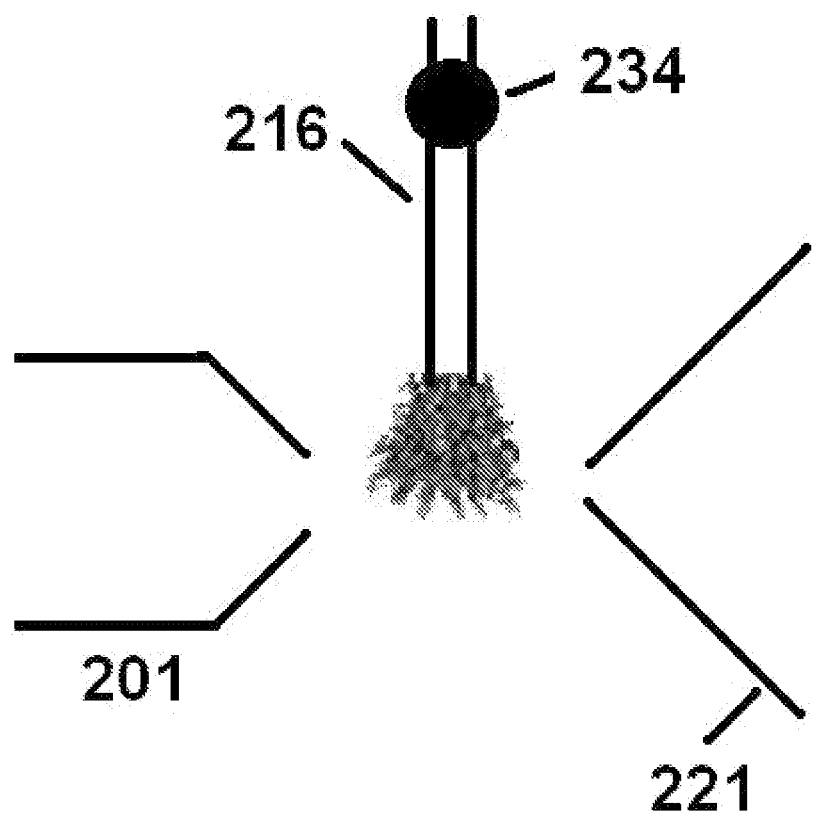
FIG. 2 shows a schematic diagram of a magnetically enabled sampling device according to an embodiment of the invention.
Figure 3:
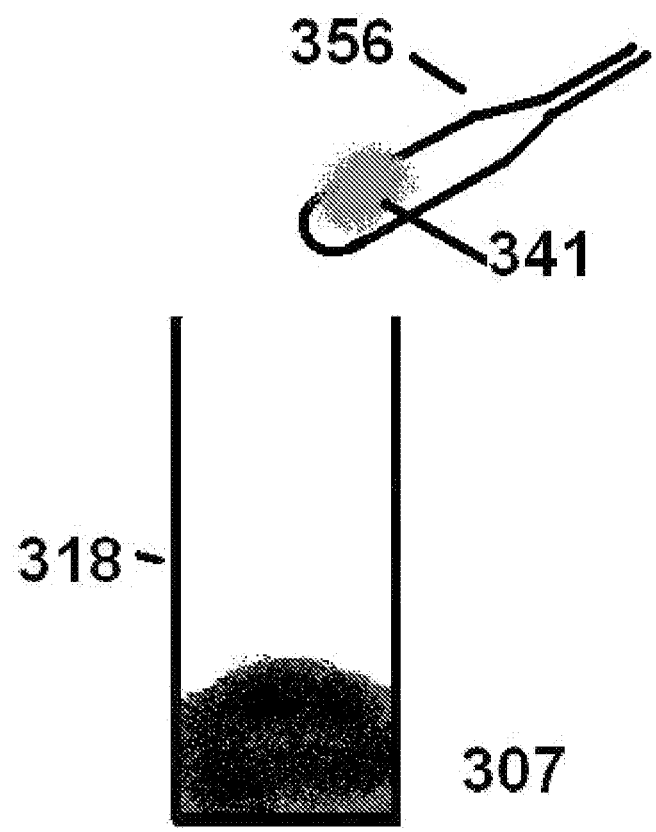
FIG. 3 shows a schematic diagram of the mixing chamber for sample preparation according to an embodiment of the invention.
Figure 4:
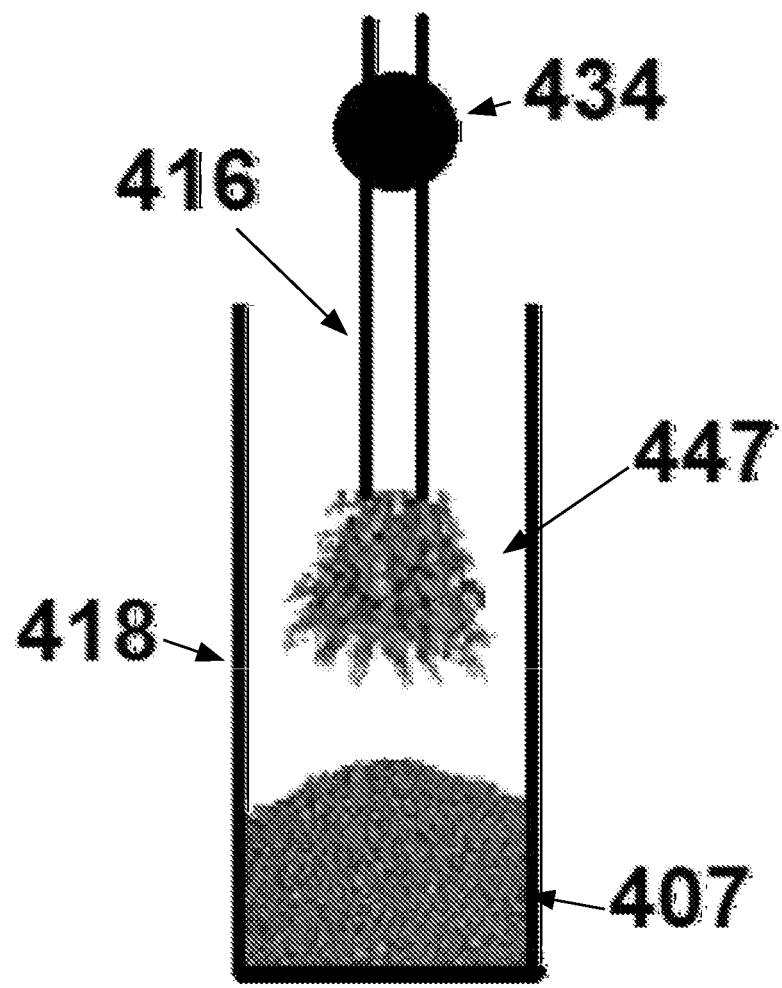
FIG. 4 shows a schematic diagram of sample loading using a magnetically enabled sampling device as shown in the mixing chamber for sample preparation as shown in FIGS. 2 and 3 according to an embodiment of the invention.
Figure 5:
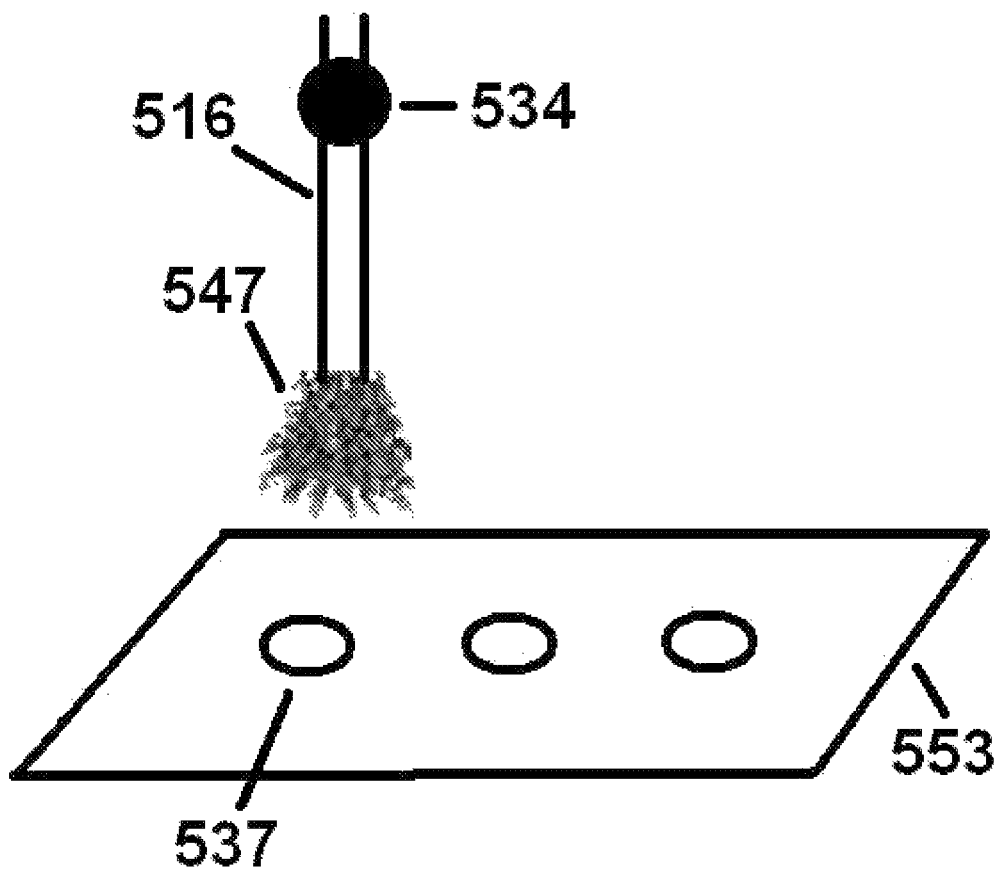
FIG. 5 shows a schematic diagram of the photograph shown in FIG. 6 where sample loading using a magnetically enabled sampling device locates sample on three sites on a surface for analysis according to an embodiment of the invention.
Figure 6:
FIG. 6 shows a photograph of sample loading which is using a magnetically enabled sampling device to locate a sample on three sites on a surface for analysis according to an embodiment of the invention.
Figure 7:
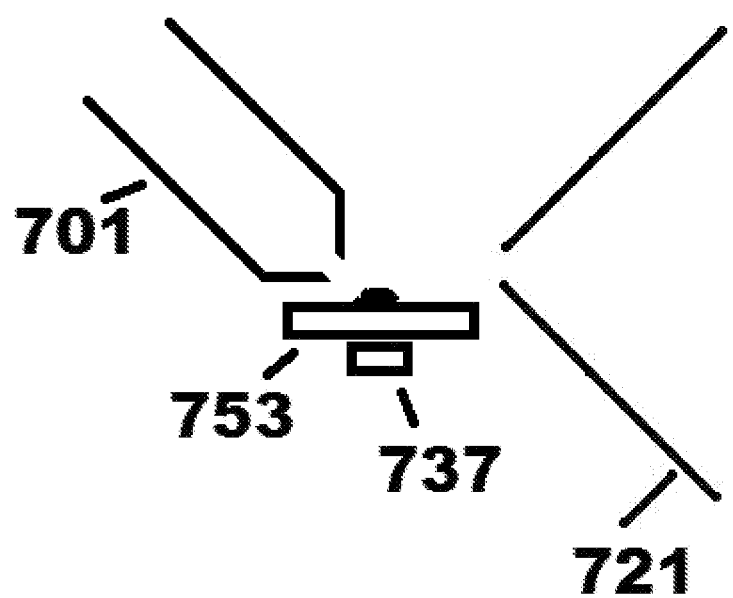
FIG. 7 shows a schematic diagram of an off axis system of analysis enabled with a spectroscopy system as shown in the photograph of FIG. 11 according to an embodiment of the invention.
Figure 8:
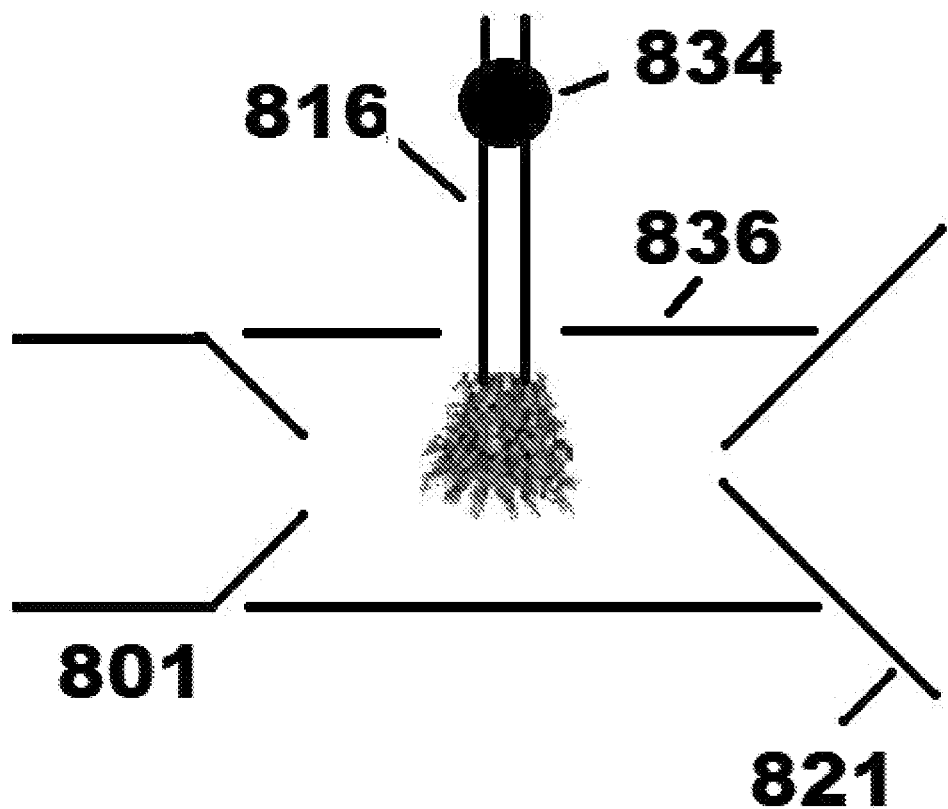
FIG. 8 shows a schematic diagram of the sampling device used to position a sample in a spectroscopy system according to an embodiment of the invention.
Figure 9:
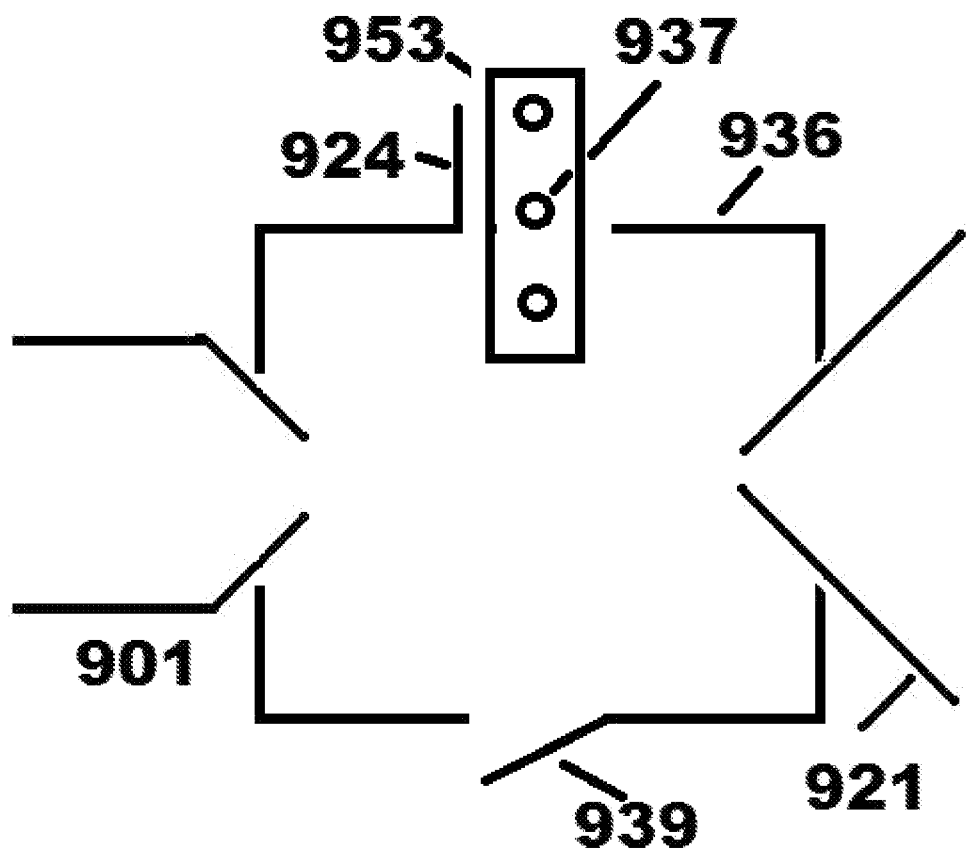
FIG. 9 shows a schematic diagram of the sampling device used to position multiple samples in a spectroscopy system according to an embodiment of the invention.
Figure 10:
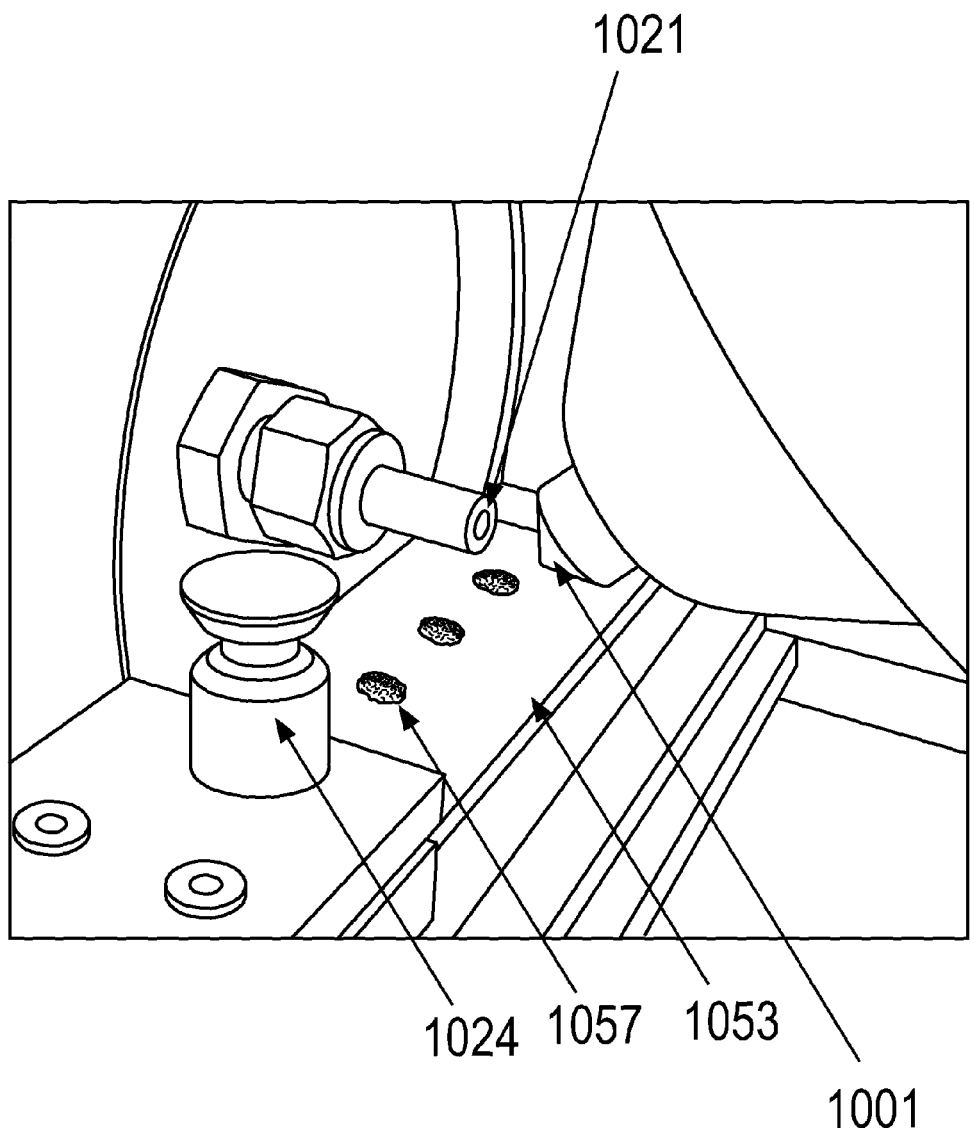
FIG. 10 shows a line drawing of an off axis system of analysis enabled with a spectroscopy system as shown in FIG. 11.
Figure 11:
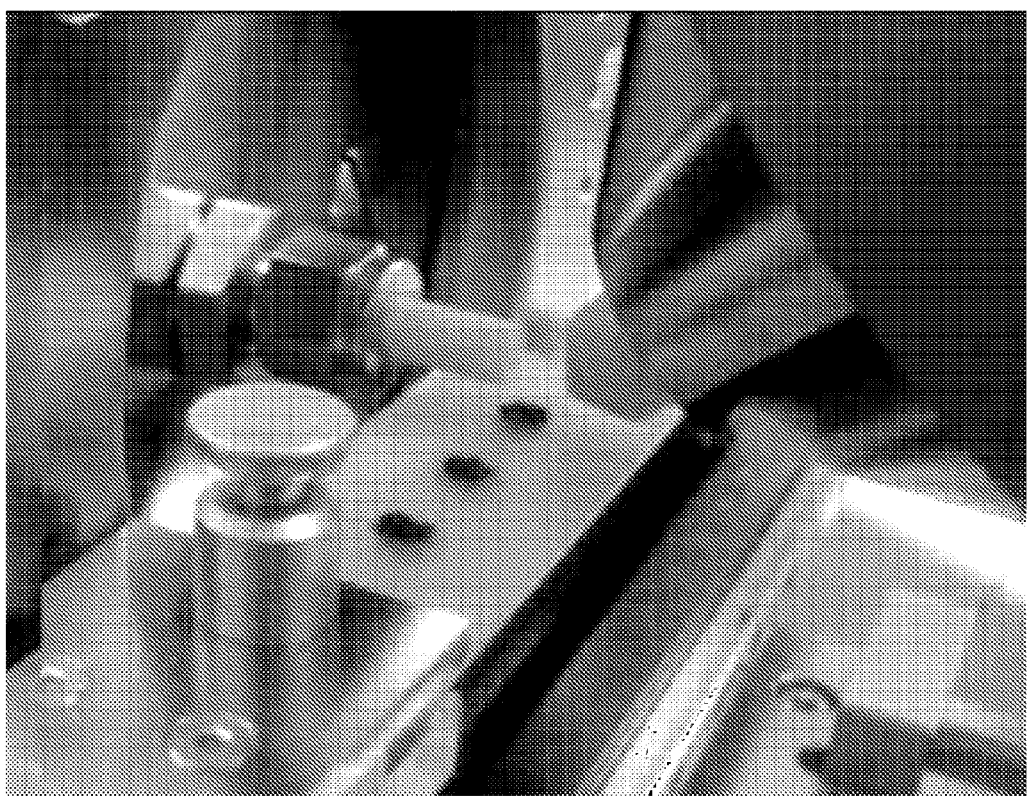
FIG. 11 shows a photograph of the off axis system of analysis device enabled with a spectroscopy system according to an embodiment of the invention.

FIG. 1 shows prior art of a desorption ionization source coupled to a mass spectrometer. In FIG. 1, the 'sampler device' 116 is a 1.4 mm outside diameter, 0.5 mm inside diameter by 6 mm long glass tube with one end sealed. The sampler device has a coating of material on its exterior surface at the closed end. The coating was generated by dissolving the sample in a solvent and then applying a solution to the sampler device 116. The device 116 is positioned between the ionization source 101 which is directing a flow of gas or liquid at the device 116. Materials desorbed from the surface are ionized and those products enter the spectrometer through an atmospheric pressure inlet 121. In various embodiments of the invention, as shown in FIG. 2, one or more small magnets or pieces of either paramagnetic or ferromagnetic susceptible metal 234 are secured to a metal rod 216 having similar dimensions to the glass rod of FIG. 1. The device 216 can be positioned between the ionization source 201 which is directing a flow of gas or liquid at the device 216. Materials desorbed from the surface can be ionized and those products can enter the spectrometer through an atmospheric pressure inlet 221. A sample of magnetic susceptible metal powder or granules co-mixed with sample powder can then be applied to the closed-end of the tube of the sampler. Preparation of the sample for analysis is depicted in FIG. 3 where a powder sample 341 represented on a common laboratory spatula 356 is added to a container 318 containing an excess of metal 307. As shown in FIG. 4 after mixing of the sample with the metal powder in the container, the metal sampler device 416 to which one or more small magnets or pieces of magnetic susceptible metal 434 have been secured can be inserted into the volume of the container 418 containing an excess of metal powder coated with the sample 407 to permit collection of a portion of the metal powder coated with sample 447. In an embodiment of the invention shown in FIG. 5 the sampler device 516 is a small magnetically susceptible piece of metal such as an iron nail to which a small magnet 534 has been positioned approximately one (1) inch above the closed end of the nail 516, referred to as a 'magnetized nail' 516. The magnetized nail 516 can be used as a sample transfer device to move sample from the container 418 shown in FIG. 4 to a surface for sampling. In FIG. 5 sample positioning of sample (mixed with metal powder 547) for analysis is facilitated by using a surface 553 under which a small magnet 537 or series of magnets can be placed in order to retain the magnetically susceptible metal powder coated with sample in position for analysis. A photograph of the device described in FIG. 5 is shown in FIG. 6. Implementation of the device of FIG. 5 with a direct analysis in real time ionization source is shown schematically in FIG. 7. FIG. 7 shows the surface 753 with magnet 737 positioned to locate sample positioned between the ionization source 701 which is directing a flow of gas or liquid at the sample. Materials desorbed from the surface are ionized and those products enter the spectrometer through an atmospheric pressure inlet 721. A line drawing of the device of FIG. 7 with a direct analysis in real time ionization source is shown in FIG. 10. A photograph of the device described in FIG. 7 is shown in FIG. 11. In an embodiment of the invention shown in FIG. 8, the end of the metal powder coated sample device 816 (utilizing a magnet 834 to hold the sample) can be positioned inside a sampling chamber 836 to allow sampling in a closed volume to protect the analyst from harmful chemicals and toxins. The end of the sampling device 816 can be positioned between the ionization source 801, which can be directing a flow of gas or liquid at the device 816. Materials desorbed from the surface can be ionized and those products enter the spectrometer through an atmospheric pressure inlet 821. In an embodiment of the invention shown in FIG. 9, the sampler device 953 can be inserted through port 924 and positioned inside a sampling chamber 936 to allow sampling in a closed volume to protect the analyst from harmful chemicals and toxins. The sampler device 953 can be positioned between the ionization source 901 which can be directing a flow of gas or liquid at the sampler device 953. Materials desorbed from the surface can be ionized and those products can enter the spectrometer through an atmospheric pressure inlet 921. Orientation of the sampler device 953 can be manipulated without concern for loss of sample since the action of the magnetic field derived from the small magnets 937 retains the sample on the surface. Once analysis is complete the sampler device 953 can exit the chamber 936 through port 939. The sample can be manipulated in the closed environment to permit analysis.

Electro-Mechanical Chamber

In an embodiment of the present invention, the 'electro-mechanical chamber' can be a cylinder having an opening through which the sampler can be inserted. The open 'electro-mechanical chamber' can be of sufficient dimension to permit insertion of a variety of objects. In an embodiment of the present invention, the open 'electro-mechanical chamber' can accept $1\times10^{-4}$ m diameter tubes. In an alternative embodiment of the present invention, the open 'electro-mechanical chamber' can accept $1\times10^{-3}$ m diameter tubes. In another embodiment of the present invention, the open 'electro-mechanical chamber' can accept $1\times10^{-2}$ m diameter tubes. In another alternative embodiment of the present invention, the open 'electro-mechanical chamber' can accept $1\times10^{-1}$ m diameter tubes. In various embodiment of the present invention, the open 'electro-mechanical chamber' can accept a non-cylindrical sampler device.

In an embodiment of the invention shown in FIG. 7 a sampler with the configuration shown in FIG. 5 can be depicted as a plate 753 with the ionization gun 701 directing species at the sample which forms ions that enter the spectrometer through aperture 721. As shown in FIG. 10 the sampler with the configuration shown in FIG. 5 is depicted as a rectangular plate 1053 with the sample mixed with metal powder 1057 has been deposited, with the ionization gun 1001 directing species at the sample which forms ions that enter the spectrometer through aperture 1021. The location of the sample mixed with metal powder 1057 in front of the ionization gun 1001 can be changed using a location locking device 1024. The rectangular plate 1053 enters the proximal end of the 'electro-mechanical chamber. FIG. 9 illustrates a series of events starting with capture of the 'sampler device' 953 in a fixed position such that the sample itself does not touch any surface of the 'electro-mechanical chamber'. The sample may be pushed through an entrance 924 and exit 939 of the chamber to permit rapid, safe detection of powder with the spectroscopy system 921. In an embodiment of the invention, a series of magnets to which a magnetically susceptible metal coated powder of interest can be positioned along a conveyor belt serves to transfer the powder coated metal to the desorption ionization region by using an electro-magnetic field. The interaction of the sample coated magnet with the electro-magnet element serves to hold the sampler in an intermediate position prior to analysis. A sampling zone 901, where the analysis occurs, can be at the distal end of the 'electro-mechanical chamber' of the desorption ionization source. At the proximal end of the 'electro-mechanical chamber a lid capable of closing and forming an airtight seal once the sampler had been placed inside the 'electro-mechanical chamber' in a fixed position. The function of the lid can be to maintain enough pressure to keep gases from escaping through the proximal end of the cylindrical 'electro-mechanical chamber'. Closure of the lid can also initiate the sampling sequence by depressing a switch or completing an electrical or optical contact, and thus connecting an initiation event marker of electrical, digital or mechanical design.

In an embodiment of the invention with the 'electro-mechanical chamber' containing the 'sampler device' closed and sealed, the composition of the chemical environment surrounding the sample can be controlled. In an embodiment of the invention, the sealed 'electro-mechanical chamber' can be used to support one or more functions selected from the group consisting of atmospheric pressure chemical ionization; negative ion chemical ionization; prevention of oxidation or reduction of the sample; or exposure of the sample to one or more other ionization sources. With the sampler under the influence of the electro-magnetic field, the sample can be positioned for desorption ionization. In the case where the sample is a large object with one or more distinct surfaces, the electro-magnetic field can be used to move the entire object in order to affect desorption of different areas of the sample by use of the electro-magnetic fields. In the case where the sample requires different ionization conditions using the same ionization source, the electro-magnetic field can be used to move the entire object in order to affect desorption of the same area of the sample with similar DART guns operated at different conditions by use of the electro-magnetic fields.

In an embodiment of the invention, after the analysis is complete and to facilitate analysis of the next sample, the electro-magnetic field can be used to expel the 'sampler device' out from the ionization region from the 'electro-mechanical chamber'. Once the analysis is complete, the electro-magnetic field can either be turned off and a spring mechanism used to release the sampler device, or the electro-magnetic field can be reversed. In an embodiment of the invention, the opening of an exit port door located at the distal end of the 'electro-mechanical chamber' can deactivate the electro-magnetic field elements and release the sampler device allowing the sample to fall under the effect of gravity through the exit port located at the distal end of the 'electro-mechanical chamber'.

In another embodiment of the invention, a series of electro-magnetic devices including rings, plates, balls, or other shapes designed to capture specific objects can be used to transport the sample into the ideal position for desorption ionization. Once the analysis is complete, the series of electro-magnetic rings can be used to eject the 'sampler device' back into the 'electro-mechanical chamber'. In another embodiment of the invention, concerted action of the electro-magnetic fields results in a high throughput apparatus for rapid sampling by desorption ionization at atmospheric pressure.

The sampler device can have a segment of metal comprised of a band of metal or a strip of metal positioned remote from the desorption ionization region. In this manner, the magnetic fields would not deflect or defocus ions that must be transferred to the spectroscopy system for analysis. In an embodiment of the invention the metal or magnets can be enclosed in the body of the sampler at a position remote from the desorption ionization region. The 'sampling device' objects can be made of glass, ceramic, plastic, wood, fabric or other suitable material shaped into tubes, rod, plates, or other objects customized for sampling. The metal pin, crimping cap, shank, brad, staple, wire or band can be inserted into or bonded to the sampling device in order to secure that sample to the sampling object.

The 'sampler device' and the 'electro-mechanical chamber' system can be automatically operated at increased sample turnaround speed without requiring an analyst or other human intervention. A significant utility of the sampler/chamber system embodied in the invention lies in unattended operation which thereby increases sampling speed.

In an embodiment of the invention a device for ionizing an analyte comprises a chamber with at least three ports, where a first port allows the analyte to enter the chamber and the chamber is adapted to mix the analyte with a material using a magnetic field source where the magnetic field source is adapted to constrain the analyte mixed with the material within the chamber. The device further comprises an atmospheric pressure ionization source adapted to be directed at the analyte mixed with the material to form analyte ions which exit out of a second port. The magnetic field source is further adapted to remove the analyte mixed with the material from the chamber through a third port to dispose of the analyte.

In an embodiment of the invention a method of ionizing a sample comprises mixing the sample with a ferromagnetic material with a lower ionization efficiency relative to the sample and constraining the sample mixed with the material using a magnetic field and generating one or more analyte ions of the sample and then using the magnetic field to dispose of the sample.

In an embodiment of the invention a kit for handling a sample for atmospheric pressure ionization comprises a vial adapted to be opened and resealed containing a material, where opening the vial and locating the sample in the vial and resealing the vial mixes the sample and the material. The kit further comprises a probe including a proximal end, a distal end, a coil situated at the distal end and a switch, where the switch is adapted to apply or discontinue an electro-magnetic field through the coil to position the material mixed with the sample onto the probe, where the probe is adapted to enter the vial and thereby position the material mixed with the sample onto the probe for removal from the vial. The kit further comprises an analysis plate with one or both a fixed magnet and an electro-magnet adapted to move the material mixed with the sample from the probe onto the analysis plate while constraining the material mixed with the sample to one or more regions on the plate for atmospheric pressure ionization.

Example embodiments of the methods, systems, and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. For example, it is envisaged that, irrespective of the actual shape depicted in the various Figures and embodiments described above, the outer diameter exit of the inlet tube can be tapered or non-tapered and the outer diameter entrance of the outlet tube can be tapered or non-tapered.

Thus, the breadth and scope of the present invention should not be limited by any of the above-described exemplary embodiments, but should be defined only in accordance with the following claims and their equivalents.

What is claimed is:

1. A device for ionizing an analyte comprising:
   a chamber with at least one port to allow the analyte to enter the chamber and adapted to mix the analyte with one or both dry powder and dry granule material;
   a magnetic field source adapted to constrain the analyte mixed with the one or both dry powder and dry granule material within the chamber; and
   an ionization source directed at the analyte within the chamber mixed with the one or both dry powder and dry granule material to form analyte ions.

2. The device of claim 1, where the position of the analyte can be adjusted relative to the ionization source prior to the ionization event.

3. The device of claim 1, where the position of the analyte can be adjusted relative to the ionization source during the ionization event.

4. The device of claim 1, where the position of the analyte can be adjusted relative to the ionization source after the ionization event.

5. The device of claim 1, where the ionization source is an atmospheric pressure ionization source.

6. The device of claim 5, where the atmospheric pressure ionization is selected from the group consisting of a Direct Ionization in Real Time source, a desorption electrospray ionization (DESI) source, an atmospheric laser desorption ionization source, a Corona discharge source, an inductively coupled plasma (ICP) source and a glow discharge source.

7. The device of claim 1, further comprising a spectroscopic analyzer adapted to analyze the analyte ions.

8. The device of claim 7, where the spectroscopic analyzer is selected from the group consisting of a mass spectrometer, Raman spectrometer, electro-magnetic absorption spectrometer, electro-magnetic emission spectrometer, surface detection spectrometer, differential scanning mobility spectrometer and ion mobility mass spectrometer.

9. The device of claim 1, where the one or both dry powder and dry granule material includes a metal with one or both a magnetic dipole moment and an inducible magnetic dipole moment.

10. The device of claim 1, where the magnetic field source is generated by one or both a magnet and an electro-magnet.

11. A kit for handling a sample for ionization comprising:
   (a) a vial adapted to be opened and resealed containing one or both dry powder and dry granule material, where opening the vial and locating the sample in the vial and resealing the vial mixes the sample and the one or both dry powder and dry granule material;
   (b) a probe adapted to enter the vial and thereby position the one or both dry powder and dry granule material mixed with the sample onto the probe for removal from the vial; and
   (c) an analysis plate with one or both a fixed magnet and an electro-magnet adapted to move the one or both dry powder and dry granule material mixed with the sample from the probe onto the analysis plate while constraining the one or both dry powder and dry granule material mixed with the sample to one or more regions on the plate for ionization.

12. The kit of claim 11, where the probe comprises a proximal end, a distal end, a coil situated at the distal end and a switch, where the switch is adapted to apply or discontinue an electro-magnetic field through the coil to position the one or both dry powder and dry granule material and the sample relative to the probe.

13. The kit of claim 12, where the one or both dry powder and dry granule material is a ferromagnetic metal.

14. A method of ionizing a sample comprising:
   (a) mixing the sample with a material consisting essentially of one or both of a dry powder and dry granule material;
   (b) controlling the position of the sample mixed with the material in a chamber using one or both an electro-mechanical force and an electric field; and
   (c) generating one or more analyte ions of the sample in the chamber while the sample remains inside the chamber.

15. The method of claim 14, where the analyte is selected from the group consisting of a powder, lyophilized sample, plant material, fine grains, and a loose substance.

16. The method of claim 14, further comprising adjusting the position of the analyte relative to the ionization source one or more of prior to, during and after the ionization event.

17. The method of claim 14, where the material and the sample are physically mixed.

18. The method of claim 14, where the one or more ions are generated at atmospheric pressure.

19. The method of claim 14, further comprising directing the ions into a spectroscopic analyzer to analyze the analyte ions.

20. The method of claim 14, where the material is selected from one or more of Fe, FeO, $FeOFe_2O_3$, $Fe_2O_3$, $MnOFe_2O_3$, $MgOFe_2O_3$, $Y_3Fe_5O_{12}$, $Fe_3O_4$, Cu, CuO, $CuOFe_2O_3$, $Cu_2O$, Al, $Al_2O_3$, Ni, NiO, $Ni_2O_3$, $Ni(OH)_2$, $NiOFe_2O_3$, Co, $NaCoO_2$ and $Co_3O_4$.

\* \* \* \* \*